United States Patent
Amarasinghe (10) Patent No.: US 7,188,620 B2
(45) Date of Patent: Mar. 13, 2007

(54) HEADGEAR

(75) Inventor: Amal Shirley Amarasinghe, Beecroft (AU)

(73) Assignee: ResMed Limited, Bella Vista (AU)

( * ) Notice: Subject to any disclaimer, the term of this patent is extended or adjusted under 35 U.S.C. 154(b) by 230 days.

(21) Appl. No.: 10/433,779

(22) PCT Filed: Dec. 12, 2001

(86) PCT No.: PCT/AU01/01607

§ 371 (c)(1),
(2), (4) Date: Nov. 13, 2003

(87) PCT Pub. No.: WO02/47749

PCT Pub. Date: Jun. 20, 2002

(65) Prior Publication Data

US 2004/0067333 A1    Apr. 8, 2004

Related U.S. Application Data

(60) Provisional application No. 60/254,537, filed on Dec. 12, 2000, now abandoned.

(51) Int. Cl.
*A62B 17/04* (2006.01)
*A61M 16/00* (2006.01)
*A63B 71/10* (2006.01)

(52) U.S. Cl. .......................... 128/201.22; 128/207.17; 2/425

(58) Field of Classification Search ........... 128/201.22, 128/202.27, 204.11, 206.13, 207.1, 207.11, 128/207.17; 2/426, 338, 428, 9, 440, 442, 2/445, 458, 452, 430

See application file for complete search history.

(56) References Cited

U.S. PATENT DOCUMENTS

| | | | |
|---|---|---|---|
| RE20,211 E | * | 12/1936 | Motsinger ............... 128/207.11 |
| 4,367,735 A | | 1/1983 | Dali et al. |
| 5,529,062 A | | 6/1996 | Byrd et al. |
| 5,542,128 A | | 8/1996 | Lomas et al. |
| 6,105,573 A | | 8/2000 | Delaplane et al. |
| 6,422,238 B1 | | 7/2002 | Lithgow |
| 2004/0112377 A1 | * | 6/2004 | Amarasinghe et al. . 128/201.22 |

FOREIGN PATENT DOCUMENTS

| | | |
|---|---|---|
| EP | 1020201 | 7/2000 |
| FR | 2 618 340 A | 1/1989 |
| WO | WO 96/25983 | 8/1996 |
| WO | WO 98/48878 | 11/1998 |

* cited by examiner

*Primary Examiner*—Teena Mitchell
*Assistant Examiner*—Shumaya Ali
(74) *Attorney, Agent, or Firm*—Nixon & Vanderhye P.C.

(57) ABSTRACT

A headgear for securing and positioning a mask suitable for the treatment of sleep disordered breathing is constructed from a composite including polyurethane foam. It includes a back portion with upper and lower straps connected to the back portion. The straps have relatively narrow strap ends the lower straps are displaced downward with respect to the back portion. A quick release mechanism near the front of the face attaches the headgear to the mask. Additional components can be attached to the straps to alter their elasticity and stiffness.

62 Claims, 5 Drawing Sheets

HEADGEAR

This is a national phase application of International Application No. PCT/AU01/01607 filed Dec. 12, 2001. which application claims priority to U.S. Patent Application No. 60/254,537, filed Dec. 12, 2000, each incorporated herein by reference in their entirety.

BACKGROUND OF THE INVENTION

1. Field of the Invention

The invention relates to headgear for use with a mask suitable for the delivery of non-invasive positive pressure ventilation and for nasal CPAP treatment of sleep disordered breathing conditions such as obstructive sleep apnea.

2. Description of Related Art

Obstructive Sleep Apnea (OSA) is a disease characterised by excessive daytime sleepiness, loud snoring and daytime irritability. Other effects of OSA can include depression, high blood pressure, serious heart conditions, sexual problems, memory lapses, intellectual deterioration and morning headaches.

The treatment of OSA by the application of nasal Continuous Positive Airway Pressure (CPAP) was invented by Sullivan and is described in U.S. Pat. No. 4,944,310 (Sullivan, assigned to ResMed Limited). The technique involves the application of a flow of pressurised breathable gas (typically room air) to either the nose or nose and mouth of a patient while they sleep. The technique is said to "splint" open the airways. Typical treatment pressures are in the range of 3 to 20 $cmH_2O$. Flows are up to approximately 200 L/min. The flow of pressurised air is produced by a blower and delivered to the patient via a patient interface. The blower and patient interface are joined by a conduit. Whilst there are other techniques for the treatment of OSA, such as surgery, the use of CPAP has become the "gold" standard.

For a particular patient, the pressure which is needed to maintain open airways can vary throughout the night and vary on different nights. U.S. Pat. No. 5,245,995 (Sullivan and Lynch, assigned to ResMed Limited) describes a method and device for varying the pressure in accordance with indications. For example, if the patient starts to snore, the pressure automatically increases, whilst in the absence of snoring, the pressure automatically decreases.

Non-Invasive Positive Pressure Ventilation (NIPPV) is another form of treatment for breathing disorders. In its most basic form, it involves a relatively higher pressure of gas being provided in the patient mask during the inspiratory phase of respiration and a relatively lower pressure or atmospheric pressure being provided in the patient mask during the expiratory phase of respiration. Typical treatment pressures are in the range of 3 to 30 $cmH_2O$.

In other NIPPV modes, the pressure can be made to vary in a complex manner throughout the respiratory cycle. For example, the pressure at the mask during inspiration or expiration can be varied through the period of treatment, as disclosed in international PCT patent application no. PCT/AU97/00631 (Berthon-Jones, assigned to ResMed Limited). In this specification, any reference to CPAP is to be understood as embracing all of the above-described forms of ventilatory treatment or assistance.

One of the earliest patient interfaces for providing CPAP treatment was constructed to include a fibreglass model of the patient's nose. The model was adhered to the patient's nose each night and removed each morning. An advantage of this patient interface included the customised fit, which assisted in a good seal between the patient interface and the patient's airways. However, the use of adhesive to secure the mask was inconvenient and not desirable.

Another suitable patient interface is described in U.S. Pat. No. 5,243,971 (Sullivan and Bruderer, assigned to the University of Sydney), entitled "Nasal Mask for CPAP having Ballooning/Moulding Seal with Wearer's Nose and Facial Contours". This patent describes a nasal mask with a soft face-contacting portion, and a rigid shell. The mask is held in position using headgear. The headgear is attached to the mask and passes around the back of the wearer's head. The patent depicts two sets of straps in the headgear. The first set comprised a pair of straps passing from the forehead region to the back of the head. The second set comprised a pair of straps passing from the nasal region of the mask to the back of the head.

Another known patient interface is the MIRAGE® nasal mask (by ResMed Ltd). This nasal mask includes a pair of headgear attachment points in the nasal region of the mask shell and a forehead support that includes another pair of headgear attachment points. The headgear includes a single piece of a soft, flexible composite fabric with a generally triangular back portion and four straps. The four straps include a pair of upper straps and a pair of lower straps connecting to the headgear attachment points on the forehead support and nasal mask shell respectively. At the end of each strap is secured a piece of hook material, which, in use, passes through a headgear attachment point and fastens on corresponding loop material on the strap. The generally triangular back portion engages the skull in the region of the occiput. The fabric stretches under a load. The base of the triangle is positioned near and generally in line with the upper straps. Each strap is approximately 2 cm wide and approximately 3 mm thick. The fabric is a composite of three layers. The inner layer, closest to the patient's head, is made from nylon. The middle layer is made from neoprene. The outer layer is made from loop material, suitable for engaging with hook fastening material such as Velcro™. The upper straps have an approximate length of 19 cm, from the end to the closest corner of the triangle, whilst the lower straps have an approximate length of 26 cm. Including the triangle, the upper and lower straps each have an approximate total length of 60.5 cm. The triangular back portion is an approximate isosceles triangle, with a base of approximately 13.5 cm and sides of approximately 9 cm.

Some patients open their mouths during sleep, which means that they may not receive the benefit of CPAP due to mouth leaks. Various solutions have been proposed for this problem. One solution is taught in U.S. Pat. No. 6,123,082 (Berthon-Jones, assigned to ResMed Limited), whereby the lips are held dosed. Another solution is to use a mask that covers both the nose and mouth of the patient. An example of a mouth and nasal mask is described in U.S. Pat. No. 5,560,354 (Berthon-Jones, Calluaud, Lynch & Hely, assigned to ResMed Limited).

Figure 1:
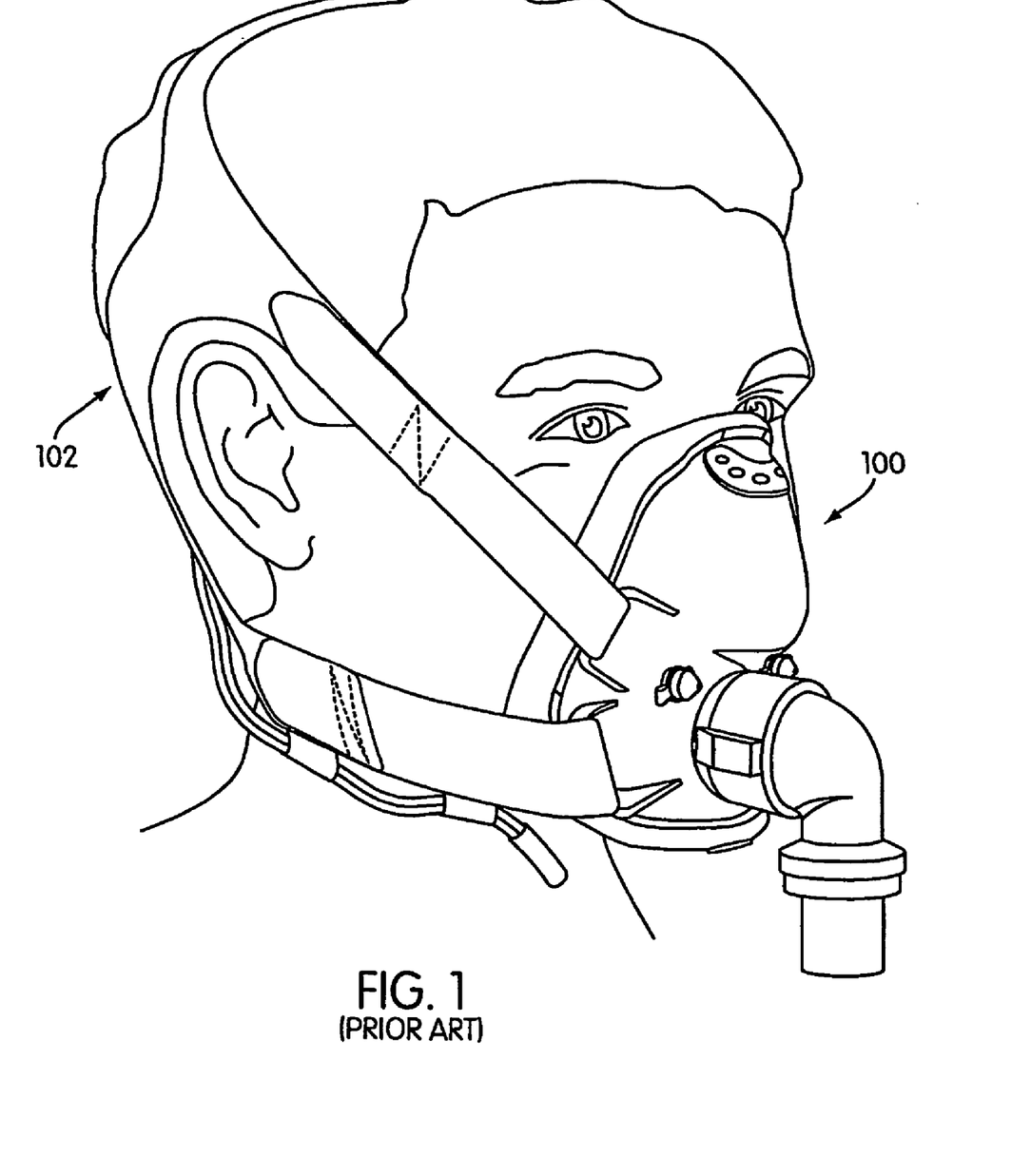
FIG. 1 shows a front three-quarter view of a MIRAGE® full-face mask and prior art headgear system in position on a patient's head.
Figure 2:
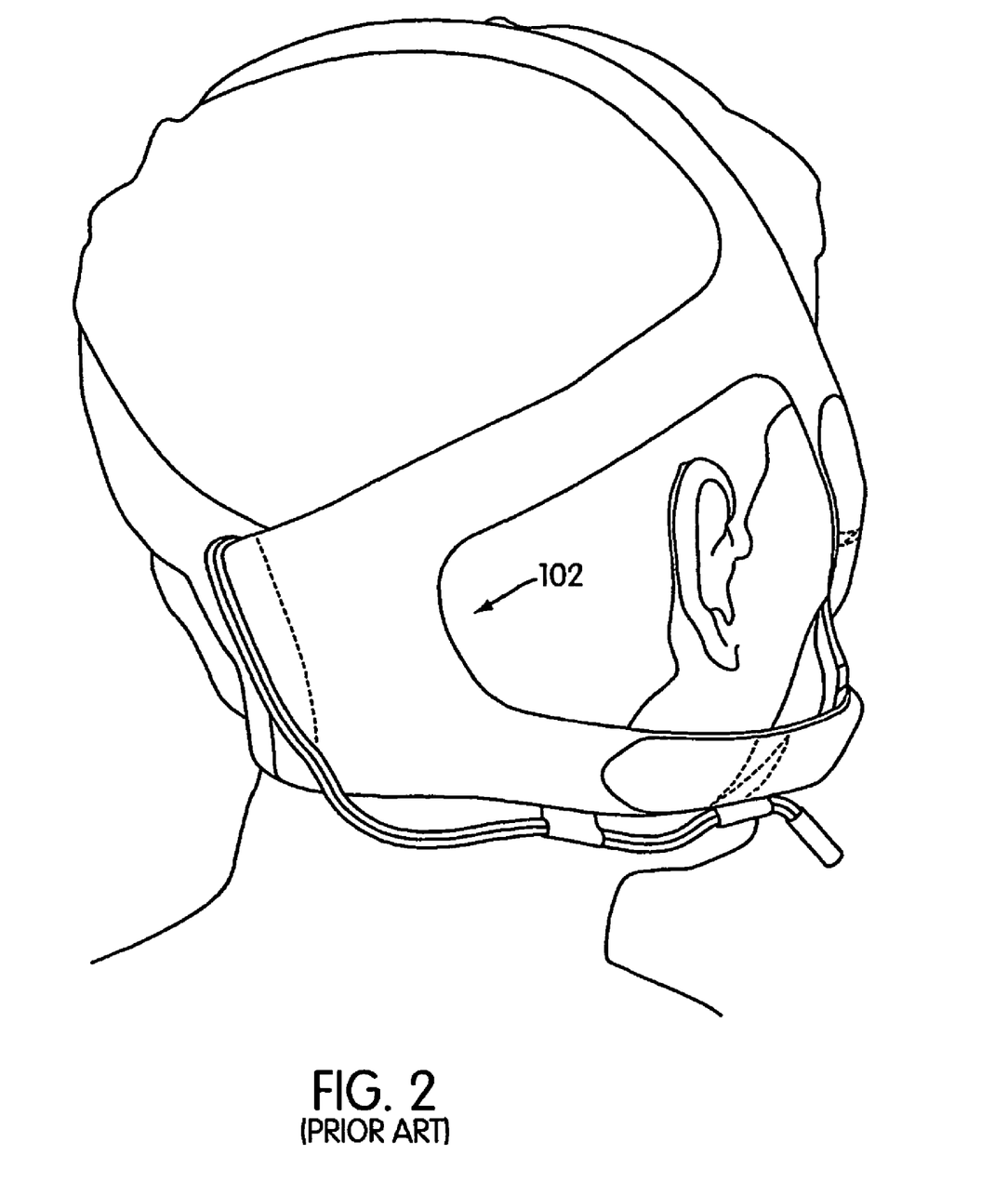
FIG. 2 shows a rear three-quarter view of a MIRAGE® full-face mask and prior art headgear system on a patient's head.
Figure 3:
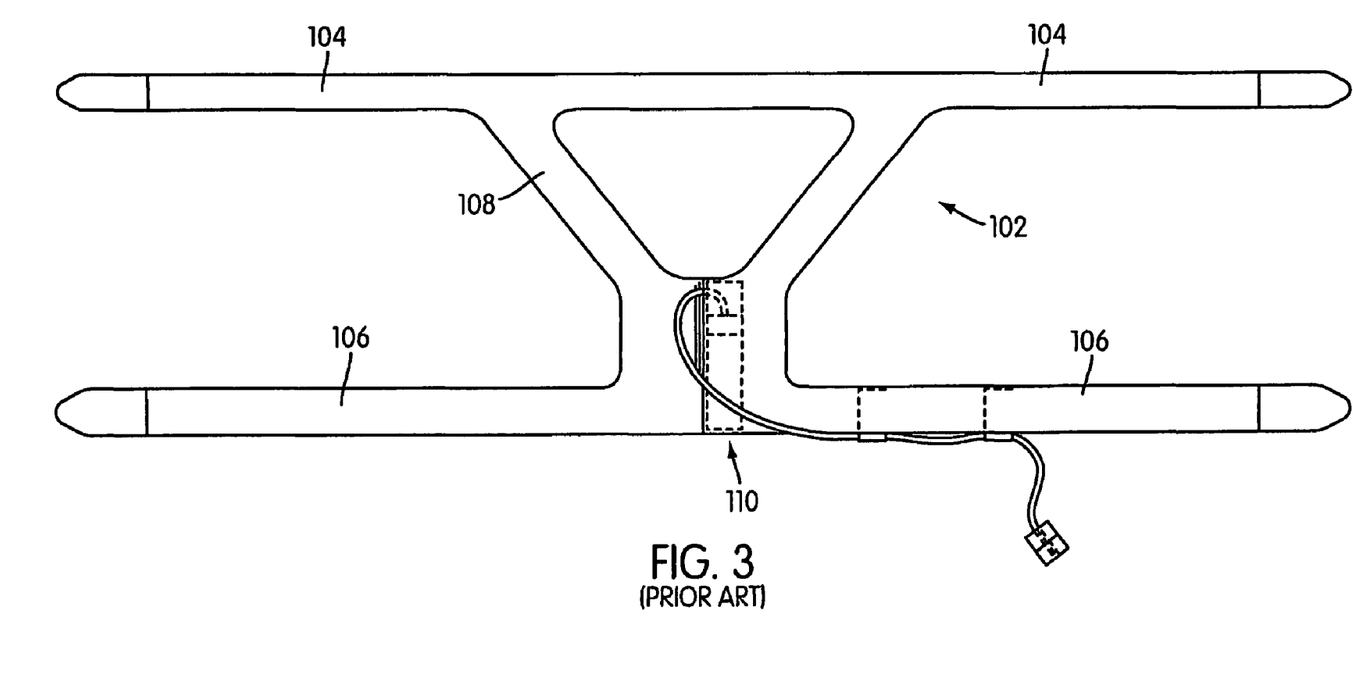
FIG. 3 shows a view of prior art full-face mask headgear laid flat.

Another suitable mask system is the MIRAGE® full-face mask (by assignee ResMed Limited). The MIRAGE® full-face mask and headgear is illustrated in FIGS. 1, 2 and 3. Suitable headgear (102) for this mask (100) is constructed from a composite material of nylon, neoprene and loop material. The headgear similarly comprises a pair of upper (104) and a pair of lower straps (106) and a generally triangular back portion (108). The upper strap has a total length of approximately 610 mm as shown in FIG. 3. The straps have an approximate width of 25 mm, however, the upper strap has an approximate width of 19 mm. The triangular region has a base of approximately 15.5 cm and two equal sides of approximately 11 cm. The upper and lower straps are approximately 192 mm apart. In addition, the headgear includes a quick release mechanism (110), as described in the pending U.S. patent application Ser. No. 09/482,718 (Lithgow, assigned to ResMed Limited). The quick release mechanism provides a "rip-chord" that can be pulled upon to separate the headgear and remove the mask in an emergency. When the headgear is positioned on the patient's head, the quick-release mechanism is situated at the back of the head and the chord runs through loops towards the front of the mask system.

Patient interface arrangements include nasal masks, nose and mouth masks, nasal prongs and nasal pillows. In all forms of patient interface used with CPAP for treating sleep disordered breathing, there is a need to counterbalance the force of the pressurised air and to correctly position the interface. Since the patient must sleep with this interface, it is important that it be comfortable. From the manufacturing and distribution channel perspectives, it is advantageous if one size of headgear fits a large range of head shapes and sizes.

It should be noted that while there are many mask and headgear arrangements available for ventilators, respirators, aviator masks and other breathing apparatus, in general, these may not be suitable for use in the treatment of sleep disordered breathing because they are not sufficiently comfortable to allow the patient to sleep.

The present invention is directed towards providing headgear for holding and securing a mask for use in the treatment of sleep disordered breathing which improves patient comfort, is long lasting and fits a wide range of head shapes and sizes.

SUMMARY OF THE INVENTION

The invention provides headgear for securing and positioning a mask suitable for the treatment of sleep disordered breathing with the following advantageous combination of features:

(i) Constructed from a composite including polyurethane foam
(ii) Relatively narrow strap ends,
(iii) Displaced lower strap,
(iv) A quick release mechanism near the front of the face; and
(v) Additional attached components to alter the elasticity and stiffness of the straps.

DETAILED DESCRIPTION OF THE INVENTION ILLUSTRATED EMBODIMENTS

The invention provides headgear (10) for securing and positioning a mask suitable for the treatment of sleep disordered breathing.

(i) Material

Figure 4:
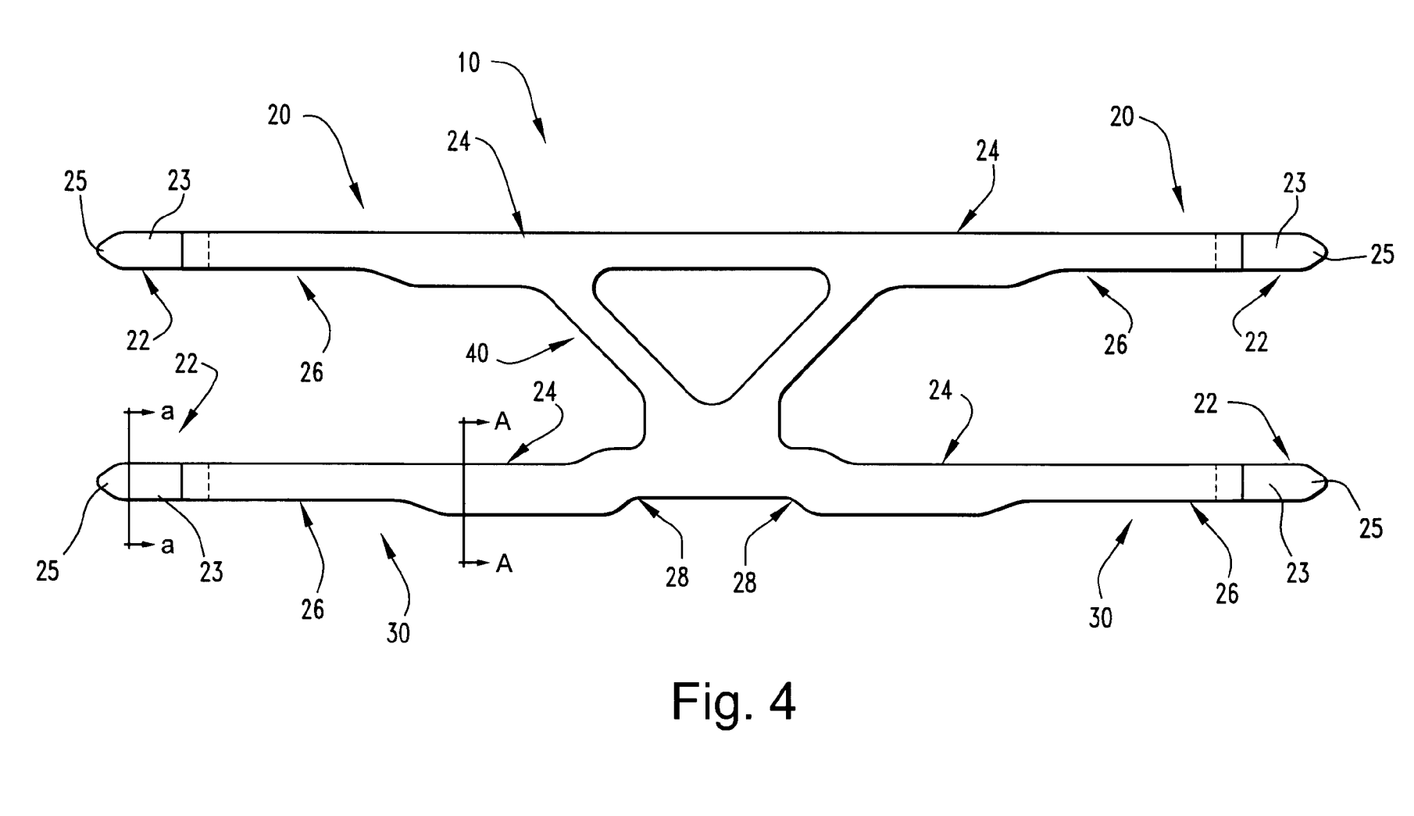
FIG. 4 shows a view of headgear according to an embodiment of the present invention.

The headgear is constructed from a composite of polyurethane foam, loop material and hook material whose shape includes a pair of upper straps (20) and lower straps (30) and a generally triangular back portion (40). A piece of hook material (22) is attached to the end of each of the four straps so that the straps may be secured to the attachment points on the mask. The end includes a main body 23 and a tapered free end portion 25.

The composite has three layers. The first layer, which in use is positioned against the head of the patient, is constructed from polyester/nylon fabric. The second, middle layer is constructed from an hypoallergenic breathable polyurethane foam. The third layer is constructed from loop material. A suitable material for constructing the composite is BREATH-A-PRENE® manufactured by ACCUMED, New York, United States of America. The total thickness of the composite is approximately 2 mm. The upper and lower pairs of straps are approximately 150 mm apart when laid flat. The upper and lower straps have an approximate total length (from the left side to the right side) of 610 mm.

The generally triangular back portion (40) of the headgear (10) is constructed and arranged to engage generally with the occiput of the patient's head in use. In use, the base of the triangle is positioned at the crown of the head, while the apex of the triangle lies generally just above the point of contact between the skull and the muscles of the neck.

(ii) Relatively Narrow Strap Ends

The headgear of the present invention is configured to minimize the discomfort associated with the use of hook material. In prior art headgear, that discomfort can arise where the hook material may be in contact with the patient's skin, say the cheek or neck regions, for extended periods of time. That undesirable contact will occur where the hook material, to some extent is not entirely located on the receiving loop material, but lies tangential to the loop material, and to some extent extends beyond the loop material and comes in contact with the patient's skin, either continuously while the headgear is in use or when it is compressed against the skin, as can occur when the patient head changes position during the sleep period.

As shown in FIG. 4, the width of each lower strap is constant for approximately half their length, forming a relatively wide portion (24), and then over a relatively short distance, changes to a narrower width for the remaining half of their length, forming a relatively narrow portion (26), terminating at the point where the hook material (22) is joined to the composite material. A characteristic of this configuration is that the point of contact where the hook material detachably binds with the strap loop material is positioned on the wide portion (24) and is wider by approximately 1 cm than the width of the engaging hook material. By adopting this configuration the target region for binding is relatively greater in the area than is the case with prior art. Moreover, the cross-sectional area (taken along Section AA) of the wide portion (or tarnet region) 24 is greater than the cross-sectional area (taken along Section a—a) of the hook material portion 22 along a majority of a length of the hook material portion. Prior art headgear includes a tapered end hook section that is of narrower width than that of the intended contact loop section of the strap. However, the prior art hook section tapered end is les than one half the length of the hook section, that is, it does not represent the majority of the length of the hook section nor does its length represent the majority of the length of the intended corresponding contact loop section (i.e., the maximum extent of the loop section covered by the hook section).

In contrast to the prior art, with the present invention the attachment of the hook material is facilitated, as relatively less precision is required in the placement of the hook section to achieve binding. This reduced dependence on precision is of advantage to all persons using the headgear and is of particular benefit to the user that may be trying to fit the headgear in a home environment and where it is not possible to directly sight the headgear components they are manipulating. Furthermore, compared to the prior art (where the hook material and the target region are of substantially the same width), this configuration reduces the chance of exposing some of the hook material to interfere with the wearer, causing discomfort and possibly skin irritation or abrasion.

(iii) Displaced Lower Strap

A length of each of the left and right lower straps is displaced vertically lower by approximately 1 cm (28). By adopting this configuration, it is possible to optimize the design of the base of the back portion so as to achieve the desired security of attachment but avoid compromising comfort in a situation where the lowest point of the headgear in the occiput region is extended to a position that is lower than is otherwise required in order to achieve a sufficiently lowest strap point. This approach avoids the prior art problem of having the headgear rear portion extending beyond what would otherwise be required and thereby engaging the sensitive area below the occipital lobe.

(iv) Quick Release Mechanism

Preferably the headgear of the present invention includes a quick release mechanism (50) (see FIG. 5), and this is especially so when the headgear is intended to be used with a mask that covers the patient's nose and mouth.

Figure 5:
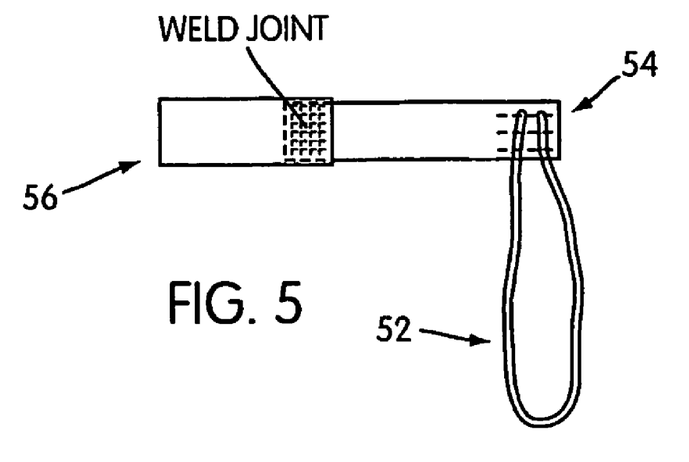
FIG. 5 shows a view of the quick release mechanism according to the present invention.

The quick-release mechanism (50) suitable for incorporation into the preferred embodiment is constructed from a sub-assembly of three components: (i) a release loop of a cord material (52), (ii) a generally rectangular length of hook material (54), and (iii) a generally rectangular length of a composite fabric (56) which can bind to the hook material, as discussed above. The sub-assembly is generally rectangular in shape and in use forms an extension of one of the lower straps. Preferably the loop cord is constructed from braided cord about 17 cm long. The cord loop (52) is sewn to one end of the length of hook material (54). The hook material (54) and composite fabric (56) are joined at the other end of the hook material (54), preferably via a weld joint. In use, the end of the hook material (54), to which is connected the loop cord (52), is secured, using the hook and loop mechanism, to the end of a modified lower strap which, in contrast to the lower straps (30) shown in FIG. 4, does not contain hook material. The other end (56) of the quick release mechanism (50) is free to be connected to a headgear attachment point on the mask shell and releasably attached to an exposed portion of the hook material (54). If it is desired to use the quick-release mechanism (50), it is convenient for the patient to pull down on the loop of braided cord (52), thereby disengaging the lower strap from the mask shell and allowing the mask to then be readily removed from the patient's face. A quick-release mechanism of this configuration may be used on headgear that is fabricated of materials and in configurations that are different to those of the type described above and as such is an invention in its own right.

(v) Altering the Stiffness and Extensibility

Figure 6A:
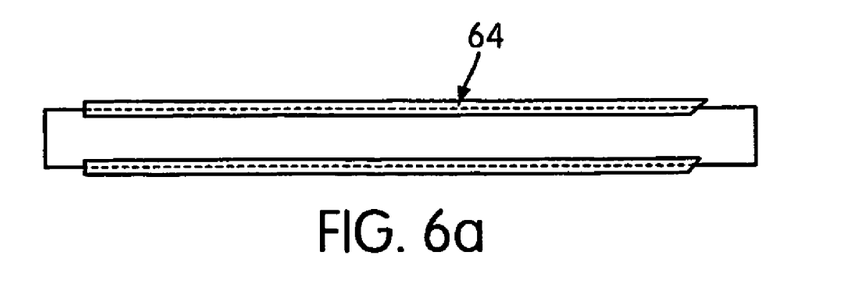
FIG. 6 shows a view of mask headgear straps in accordance with the present invention laid flat.

In one form of the invention, the extensibility of the straps can be altered by attaching lengths of generally inextensible material (62) such as cotton or silk to the straps, as shown in FIG. 6a. The effect of this arrangement is to make the headgear less extensible along the length of the straps than in a vertical direction. In a preferred embodiment, lengths of cotton are sewn to the straps.

Figure 6B:
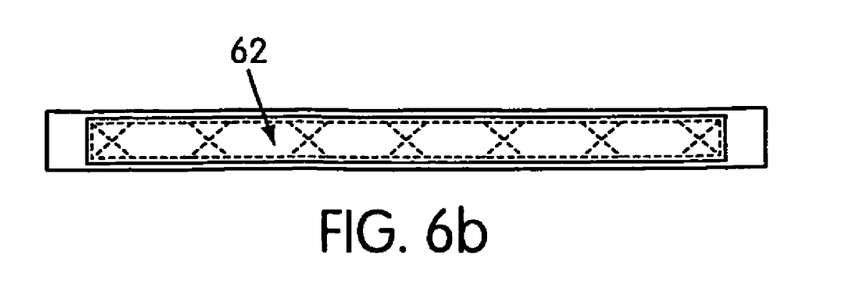

In another form of the invention, the stiffness of the straps can be altered by attaching stiffening material (64) to the top and bottom edge of the straps, as shown in FIG. 6b. Alternatively, or in addition, the strap may be stiffened by any other suitable means including by adding stitching as lines, in a criss-cross pattern, or both. This makes the headgear less "floppy" and more convenient to put on the head of a wearer.

In another form of the invention, the headgear is constructed from an anisotropic material that is more extensible in a first direction than in a direction at an angle of 90 degrees to the first direction. This enables the headgear to be cut from a single piece of composite material and yet have different extensibilities in different directions. Preferably, the headgear will be more extensible in a vertical direction than in a horizontal direction. Hence the upper and lower straps will be less extensible in a direction along their length than in a direction along their width. This means that the back portion of the headgear can be more extensible in a direction from the base of the skull to the crown, than in a direction at right angles to that direction.

What is claimed is:

1. A headgear for securing and positioning a mask suitable for the treatment of sleep disordered breathing, comprising:
   a back portion;
   a pair of elongated upper straps provided to the back portion on opposing sides of the back portion and extending away from the back portion, each of the upper straps having a hook material portion with a main body and a tapered free end; and
   a pair of elongated lower straps provided to the back portion below the upper straps on opposing sides of the back portion and extending away from the back portion, each of the lower straps having a hook material portion with a main body and a tapered free end;
   wherein a portion of each strap adjacent the back portion and extending approximately half a length of the strap has a first width comprising a loop material portion and the hook material portion of each strap has a second width substantially narrower than the first width.

2. The headgear of claim 1, wherein each lower strap angles downward from the back portion at a position near the back portion to displace a length of each lower strap outboard from the angled portion downward with respect to the back portion.

3. The headgear of claim 2, wherein at least one of the straps is constructed of an extensible material and a generally inextensible material is attached to that strap to make the strap generally inextensible in a direction of its length.

4. The headgear of claim 1, wherein, at least one of the straps is constructed of an anisotropic material such that the strap is generally inextensible in a direction along its length and extensible in a direction along its width.

5. The headgear of claim 1, wherein the second width is narrower than the first width by approximately 1 cm.

6. The headgear of claim 1, wherein the second width is narrower than the first width by at least 1 cm.

7. The headgear of claim 1, wherein the bank portion, the pair of upper straps and the pair of lower straps are formed as a substantially contiguous, one piece unit.

8. The headgear of claim 1, wherein a width of the loop material portion varies along a length of each of the upper and lower straps.

9. The headgear of claim 8, wherein the width of the loop material portion oriented towards the main body of the hook material portion is less than the width of the loop material portion oriented towards the back portion.

10. A mask comprising:
a frame supporting a soft face-contacting portion, the frame having at a first pair of attachment points and a second pair of attachment points, both adjacent the soft face-contacting portion, and
the headgear of claim 1,
wherein the pair of upper straps is adapted to be coupled to the first pair of attachment points and the pair of lower straps is adapted for coupling to the second pair of attachments points.

11. A headgear for securing and positioning a mask suitable for the treatment of sleep disordered breathing, comprising:
a back portion;
a pair of elongated upper straps provided to the back portion on opposing sides of the back portion and extending away from the back portion, each of the upper straps having a hook material portion with a main body and a tapered free end; and
a pair of elongated lower straps provided to the back portion below the upper straps on opposing sides of the back portion and extending away from the back portion, each of the lower straps having a hook material portion with a main body and a tapered free end;
wherein a portion of each strap adjacent the back portion has a first width comprising a loop material portion and the hook material portion of each strap has a second width substantially narrower than the first width,
wherein the headgear is formed of a composite having a first layer, to be positioned against the head of the patient, constructed from a polyester/nylon fabric, a second, middle layer constructed from a foam material and a third layer constructed from said loop material adapted to engage and attach to said hook material.

12. The headgear of claim 11, wherein the foam comprises hypoallergenic breathable polyurethane.

13. The headgear of claim 11, wherein the back portion, the pair of upper straps and the pair of lower straps are formed as a substantially contiguous, one piece unit.

14. The headgear of claim 11, wherein a width of the loop material portion varies along a length of each of the upper and lower straps.

15. The headgear of claim 14, wherein the width of the loop material portion oriented towards the main body of the hook material portion is less than the width of the loop material portion oriented towards the back portion.

16. A mask comprising:
a frame supporting a soft face-contacting portion, the frame having at a first pair of attachment points and a second pair of attachment points, both adjacent the soft face-contacting portion, and
the headgear of claim 11,
wherein the pair of upper straps is adapted to be coupled to the first pair of attachment points and the pair of lower straps is adapted for coupling to the second pair of attachments points.

17. A headgear for securing and positioning a mask suitable for the treatment of sleep disordered breathing, comprising:
a back portion;
a pair of elongated upper straps provided to the back portion on opposing sides of the back portion and extending away from the back portion, each of the upper straps having (i) a hook material portion with a main body and a tapered free end and (ii) a relatively wider loop material portion positioned between the respective free end and the back portion; and
a pair of elongated lower straps provided to the back portion below the upper straps on opposing sides of the back portion and extending away from the back portion, each of the lower straps having (i) a hook material portion with a main body and a tapered free end and (ii) a relatively wider loop material portion positioned between the respective free end and the back portion;
wherein each lower strap angles downward from the back portion at a position near the back portion to displace a length of each lower strap outboard from the angled portion downward with respect to the back portion.

18. The headgear of claim 17, wherein a portion of each lower strap outboard from the angled portion is lower than a lowest portion of a central region of the back portion.

19. The headgear of claim 18, wherein at least one of the straps is constructed of an extensible material and a generally inextensible material is attached to that strap to make the strap generally inextensible in a direction of its length.

20. The headgear of claim 18, wherein, at least one of the straps is constructed of an anisotropic material such that the strap is generally inextensible in a direction along its length and extensible in a direction along its width.

21. The headgear of claim 17, wherein the length of each lower strap outboard from the angled portion is displaced downward with respect to the back portion by approximately 1 cm.

22. The headgear of claim 18, wherein the length of each lower strap outboard from the angled portion is displaced downward with respect to the back portion by at least 1 cm.

23. The headgear of claim 17, wherein the back portion, the pair of upper straps and the pair of lower straps are formed as a substantially contiguous, one piece unit.

24. The headgear of claim 17, wherein a width of the loop material portion varies along a length of each of the upper and lower straps.

25. The headgear of claim 24, wherein the width of the loop material portion oriented towards the main body of the hook material portion is less than the width of the loop material portion oriented towards the back portion.

26. A mask comprising:
a frame supporting a soft face-contacting portion, the frame having at a first pair of attachment points and a second pair of attachment points, both adjacent the soft face-contacting portion, and
the headgear of claim 17,
wherein the pair of upper straps is adapted to be coupled to the first pair of attachment points and the pair of lower straps is adapted for coupling to the second pair of attachments points.

27. A headgear for securing and positioning a mask suitable for the treatment of sleep disordered breathing, comprising:
a back portion;
a pair of elongated upper straps provided to the back portion on opposing sides of the back portion and extending away from the bark portion, each of the upper straps having (i) a hook material portion with a main body and a tapered free end and (ii) a substantially wider loop material portion positioned between the respective free end and the back portion; and
a pair of elongated lower straps provided to the back portion below the upper straps on opposing sides of the back portion and extending away from the back portion, each of the lower straps having (i) a hook material portion with a main body and a tapered free end and (ii)

a substantially wider loop material portion positioned between the respective free end and the back portion, wherein the headgear is formed of a composite having a first layer, to be positioned against the head of the patient, constructed from a polyester/nylon fabric, a second, middle layer constructed from a foam material and a third layer constructed from said loop material adapted to engage and attach to said hook material.

28. The headgear of claim 27, wherein the foam comprises hypoallergenic breathable polyurethane.

29. The headgear of claim 27, wherein the back portion, the pair of upper straps and the pair of lower straps are formed as a substantially contiguous, one piece unit.

30. The headgear of claim 27, wherein a width of the loop material portion varies along a length of each of the upper and lower straps.

31. The headgear of claim 30, wherein the width of the loop material portion oriented towards the main body of the hook material portion is less than the width of the loop material portion oriented towards the back portion.

32. A mask comprising:
a frame supporting a soft face-contacting portion, the frame having at a first pair of attachment points and a second pair of attachment points, both adjacent the soft face-contacting portion, and the headgear of claim 27, wherein the pair of upper straps is adapted to be coupled to the first pair of attachment points and the pair of lower straps is adapted for coupling to the second pair of attachments points.

33. A headgear for securing and positioning a mask suitable for the treatment of sleep disordered breathing, comprising:
a back portion; and
a pair of elongated straps provided to the back portion on opposing sides of the back portion and extending away from the back portion, each strap having a loop portion positioned along an external surface of its length and a hook portion located near or at a free end thereof for releasably attaching to the loop portion;
wherein a width of at least one of the pair of straps along the loop portion to which the hook portion releasably attaches is sufficiently wider than a maximum width of the hook portion so that when the hook portion is attached to the loop portion, the at least one strap shields a user's face from contact with the hook portion.

34. The headgear of claim 33, wherein the width of the strap along the loop portion to which the hook portion releasably attaches is wider than the hook portion by approximately 1 cm.

35. The headgear of claim 33, wherein the width of the strap along the loop portion to which the hook portion releasably attaches is wider than the hook portion by at least 1 cm.

36. The headgear of claim 33, wherein the back portion and the pair of straps are formed as a substantially contiguous, one piece unit.

37. The headgear of claim 33, wherein a width of the loop portion varies along a length of each of the pair of straps.

38. The headgear of claim 37, wherein the width of the loop portion oriented towards the hook portion is less than the width of the loop portion oriented towards the back portion.

39. A mask comprising:
a frame supporting a soft face contacting portion, the frame including at least a pair of attachment points adjacent the soft face-contacting portion; and
the headgear of claim 33,
wherein the pair of straps is adapted to be coupled to the pair of attachments points.

40. The mask according to claim 33, wherein the back portion includes strap portions that define an opening arranged to engage the patient's occiput.

41. The mask according to claim 33, wherein each of the strap portions includes multiple layers.

42. A headgear for securing and positioning a mask suitable for the treatment of sleep disordered breathing, comprising:
a back portion arranged to engage with an occiput of a patient's head in use; and
first and second elongated straps provided to and extending from the back portion, the first elongated strap being positioned on one portion of the back portion and the second elongated strap being positioned on an opposite portion of the back portion, the first and second straps having a hook and loop fastening arrangement including a hook material portion positioned at an end of each of the first and second straps for coupling with the mask, each said end having a main body and a tapered free end portion, wherein:
each of the first and second straps includes a loop material portion positioned between the free end and the back portion, the loop material portion having a first width, and
the main body of the hook material portion of each of the first and second straps has a second width that is narrower than the first width.

43. The headgear of claim 42, wherein at least the back portion of the headgear is formed of a composite having a first layer, to be positioned against the head of the patient, constructed from a polyester/nylon fabric, a second middle layer constructed from an hypoallergenic breathable polyurethane foam and a third layer.

44. The headgear of claim 42, wherein the second width is narrower than the first width by approximately 1 cm.

45. The headgear of claim 42, wherein the back portion includes an open space defined by the strap material of the back portion.

46. The headgear of claim 42, wherein the headgear is formed of a composite having at least a first layer, to be positioned against the head of the patient and constructed from a polyester/nylon fabric, and a second layer.

47. The headgear of claim 42, wherein the first and second straps and the back portion are formed as a substantially contiguous, one piece unit.

48. The headgear of claim 42, wherein a width of the loop material portion varies along a length of each of the first and second straps.

49. The headgear of claim 48, wherein the width of the loop material portion oriented towards the main body of the hook material portion is less than the width of the loop material portion oriented towards the back portion.

50. A mask comprising:
a frame supporting a soft face contacting portion, the frame including at least a pair of attachment points adjacent the soft face-contacting portion; and
the headgear of claim 42,
wherein the first and second straps are adapted to be coupled to the pair of attachments points.

51. The mask according to claim 42, wherein the bank portion includes strap portions that define an opening arranged to engage the patient's occiput.

52. The mask according to claim 42, wherein each of the strap portions includes multiple layers.

53. A headgear for securing and positioning a mask suitable for the treatment of sleep disordered breathing, comprising:
   a back portion arranged to engage with an occiput of a patient's head in use; and
   first and second elongated straps provided to and extending from the back portion, the first elongated strap being positioned on one portion of the back portion and the second elongated strap being positioned on an opposite portion of the back portion, wherein:
   the first and second straps have a hook and loop fastening arrangement including a hook material portion positioned at or near an end of each of the first and second straps, each of the first and second straps being couplable to the mask via the hook and loop fastening arrangement, wherein;
   each of the first and second straps defines a target region for binding with the hook material portion, said target region comprising a loop material portion positioned between the end and the back portion, said target region having a width that is greater than a maximum width of the hook material portion so as to reduce the chance of exposing the hook material portion to interfere with the patient in use.

54. The headgear of claim 53, wherein the maximum width of the hook material portion is narrower than the width of the target region by approximately 1 cm.

55. The headgear of claim 53, wherein the back portion includes an open space defined by strap material of the back portion.

56. The headgear of claim 53, wherein the headgear is formed of a composite having at least a first layer, to be positioned against the head of the patient and constructed from a polyester/nylon fabric, and a second layer.

57. The headgear of claim 53, wherein the first and second straps and the back portion are formed as a substantially contiguous, one piece unit.

58. The headgear of claim 53, wherein a width of the loop material portion varies along a length of each of the first and second straps.

59. The headgear of claim 58, wherein the width of the loop material portion oriented towards the hook material portion is less than the width of the loop material portion oriented towards the back portion.

60. A mask comprising:
   a frame supporting a soft face contacting portion, the frame including at least a pair of attachment points; and
   the headgear of claim 53,
   wherein the first and second straps are adapted to be coupled to the pair of attachments points.

61. The mask according to claim 53, wherein the back portion includes strap portions that define an opening arranged to engage the patient's occiput.

62. The mask according to claim 53, wherein each of the strap portions includes multiple layers.

* * * * *

UNITED STATES PATENT AND TRADEMARK OFFICE
CERTIFICATE OF CORRECTION

| | |
|---|---|
| PATENT NO. | : 7,188,620 B2 |
| APPLICATION NO. | : 10/433779 |
| DATED | : March 13, 2007 |
| INVENTOR(S) | : Amarasinghe |

It is certified that error appears in the above-identified patent and that said Letters Patent is hereby corrected as shown below:

Col. 6, Claim 7, line 1, should read as follows:

7.  The headgear of claim 1, wherein the back portion, the pair of upper straps and the pair of lower straps are formed as a substantially contiguous, one piece unit.

Col. 11, Claim 51, line 1, should read as follows:

51.  The mask according to claim 42, wherein the back portion includes strap portions that define an opening arranged to engage the patient's occiupt.

Signed and Sealed this
Eleventh Day of September, 2012

David J. Kappos
*Director of the United States Patent and Trademark Office*